(12) United States Patent
Motaganahalli

(10) Patent No.: US 9,398,965 B2
(45) Date of Patent: *Jul. 26, 2016

(54) INTRAVASCULAR SHUNT FOR TRAUMATIZED ARTERIES

(71) Applicant: INDIANA UNIVERISTY RESERACH AND TECHNOLOGY CORPORATION, Indianapolis, IN (US)

(72) Inventor: Raghu L. Motaganahalli, Carmel, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/878,143

(22) Filed: Oct. 8, 2015

(65) Prior Publication Data

US 2016/0058586 A1 Mar. 3, 2016

Related U.S. Application Data

(63) Continuation of application No. 14/085,528, filed on Nov. 20, 2013, now Pat. No. 9,180,033.

(60) Provisional application No. 61/728,433, filed on Nov. 20, 2012.

(51) Int. Cl.
*A61M 5/00* (2006.01)
*A61F 2/848* (2013.01)
(Continued)

(52) U.S. Cl.
CPC .............. *A61F 2/848* (2013.01); *A61B 17/0057* (2013.01); *A61B 17/12036* (2013.01); *A61B 17/12136* (2013.01); *A61F 2/94* (2013.01); *A61F 2/95* (2013.01); *A61M 1/3655* (2013.01); (Continued)

(58) Field of Classification Search
CPC ........ A61F 2/95; A61F 2/07; A61F 2202/061; A61M 1/3655; A61B 17/11; A61B 17/0057; A61B 17/12036; A61B 17/12136; A61B 2017/00659; A61B 2017/12127; A61B 2017/1107
USPC ...................... 604/8, 9, 96.01, 174, 175, 264; 623/1.11, 1.3, 1.31, 1.36, 1.37, 23.64, 623/23.7; 606/196, 191, 153–158
See application file for complete search history.

(56) References Cited

U.S. PATENT DOCUMENTS 3,435,824 A 4/1969 Gamponia
3,516,408 A 6/1970 Montanti
(Continued)

FOREIGN PATENT DOCUMENTS

EP 2110151 A1 10/2009
EP 2508221 A1 10/2012
WO WO95/12368 A1 5/1995

*Primary Examiner* — Philip R Wiest
(74) *Attorney, Agent, or Firm* — Faegre Baker Daniels LLP

(57) ABSTRACT

The present invention relates to a catheter assembly including a catheter body, a first and a second set of a plurality of fenestrations, a first and a second inflatable device, a first and a second pleat, at least one obstructing stop near each end portion of the catheter body, and a first and a second flexible tube connected to the first and the second inflatable device. The catheter assembly further includes a pumping device in communication with the first and the second inflatable device via the first and the second flexible tube. The catheter assembly is used to restore blood flow to a traumatized blood vessel.

20 Claims, 5 Drawing Sheets

(51) Int. Cl.
  *A61F 2/95* (2013.01)
  *A61M 1/36* (2006.01)
  *A61B 17/00* (2006.01)
  *A61B 17/12* (2006.01)
  *A61F 2/94* (2013.01)

(52) U.S. Cl.
  CPC .................. *A61B 2017/00659* (2013.01); *A61B 2017/12127* (2013.01); *A61F 2002/8486* (2013.01)

(56) References Cited

U.S. PATENT DOCUMENTS

| | | | |
|---|---|---|---|
| 3,991,767 A | 11/1976 | Miller, Jr. et al. | |
| 4,230,119 A | 10/1980 | Blum | |
| 4,721,109 A * | 1/1988 | Healey | A61B 17/11 606/156 |
| 5,342,306 A | 8/1994 | Don Michael | |
| 5,380,284 A | 1/1995 | Don Michael | |
| 5,820,595 A | 10/1998 | Parodi | |
| 5,919,163 A | 7/1999 | Glickman | |
| 6,017,352 A | 1/2000 | Nash et al. | |
| 6,575,932 B1 | 6/2003 | O'Brien et al. | |
| 7,758,542 B2 | 7/2010 | Whalen et al. | |
| 7,780,628 B1 | 8/2010 | Keren et al. | |
| 7,819,841 B2 | 10/2010 | Horrigan | |
| 7,914,503 B2 | 3/2011 | Goodson, IV et al. | |
| 8,007,464 B2 * | 8/2011 | Gellman | A61B 25/0097 604/101.01 |
| 9,180,033 B2 * | 11/2015 | Motaganahalli | A61M 1/3655 |
| 2008/0294084 A1 * | 11/2008 | Buckman | A61B 17/11 604/8 |
| 2010/0049162 A1 | 2/2010 | Hameed | |

* cited by examiner

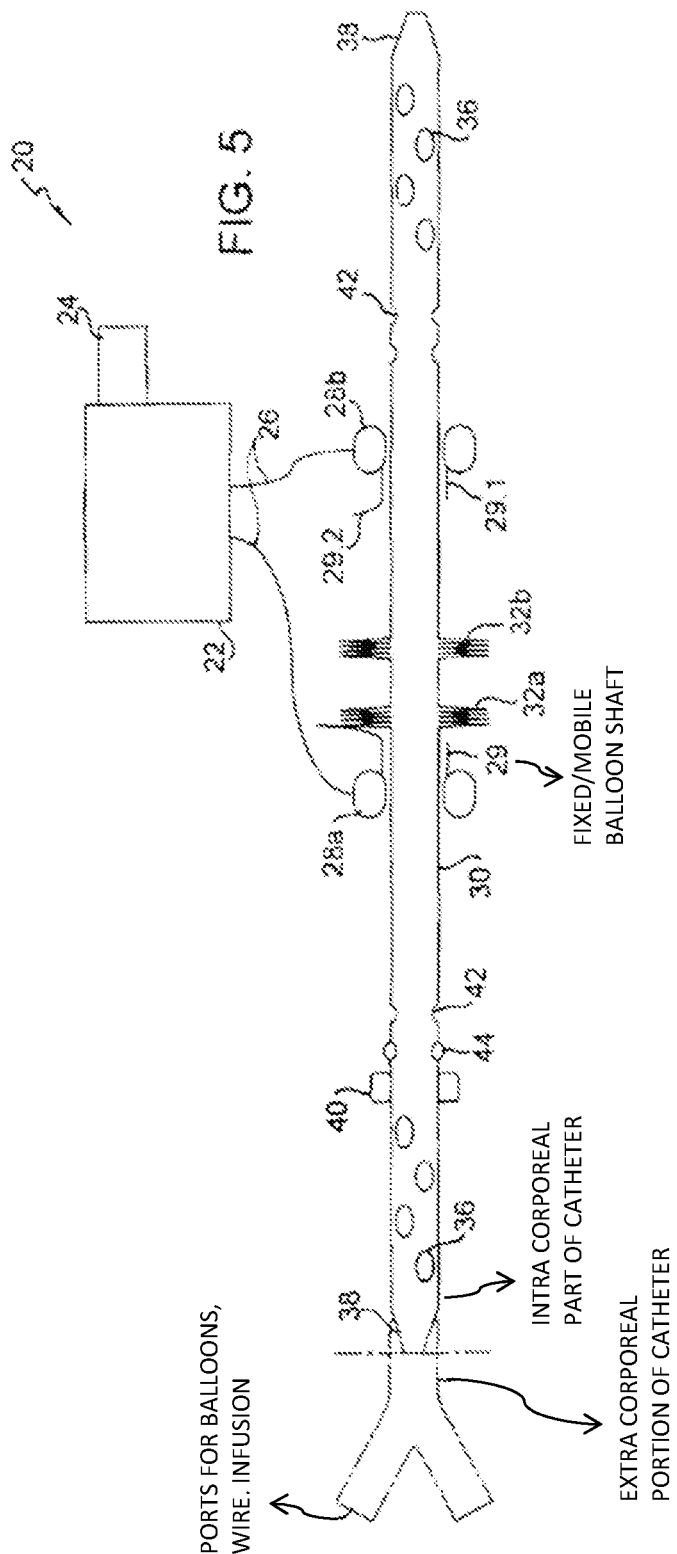

INTRAVASCULAR SHUNT FOR TRAUMATIZED ARTERIES

CROSS REFERENCE TO RELATED APPLICATIONS

This application is a Continuation of U.S. patent application entitled INTRAVASCULAR SHUNT FOR TRAUMATIZED ARTERIES, Ser. No. 14/085,528 filed Nov. 20, 2013 which is a non-provisional of U.S. Provisional Patent Application entitled INTRAVASCULAR SHUNT FOR TRAUMATIZED ARTERIES, Ser. No. 61/728,433 filed Nov. 20, 2012 the entire disclosures of which are hereby explicitly incorporated by reference herein.

FIELD OF THE INVENTION

The present invention relates to a catheter and a method of treating traumatized arteries using the catheter.

BACKGROUND OF THE INVENTION

Hemorrhage remains a leading cause of death in trauma patients. Vascular injuries, which threaten both life and limb, have always constituted a serious problem in the surgical management of traumatic conditions. Intravascular shunts have been used to restore and maintain arterial flow during the repair of complex injuries, especially those involving extensive bony or soft tissue destruction.

It is an object of the present invention, therefore, to provide a catheter assembly used as a shunt for restoring blood flow in a traumatized blood vessel. It is a further object of the present invention to provide a method for restoring blood flow to a traumatized blood vessel using a catheter assembly.

SUMMARY OF THE INVENTION

The present invention relates to a catheter assembly for restoring blood flow to a traumatized blood vessel, comprising: a catheter body, in a tubular shape, comprising: a first and a second tip, each configured to permit insertion into a blood vessel without damaging an inner wall of a blood vessel lumen; a first and a second set of a plurality of fenestrations, disposed proximate to each tip extending a length of the catheter body away from each tip towards a center portion of the tubular catheter body; a first and a second inflatable device, placed circumferentially and longitudinally about the catheter body, configured such that when uninflated each is capable of sliding over a section of the catheter body, and when inflated an inner annulus of each presses against an outer perimeter of the catheter body; a first and a second pleat, spaced apart by a midsection, located in the center portion of the catheter body between the first and the second inflatable device; at least one obstructing stop, located on the outer perimeter of the catheter body in a section longitudinally adjacent to each of the first and the second set of the plurality of fenestrations towards the center portion, to obstruct the first or the second inflatable device from sliding over the first or second set of a plurality of fenestrations proximate to the first or the second tip of the catheter body, and a first and a second flexible tube connected to the first and the second inflatable device, respectively, and adapted to allow fluid communication from a pumping device with the first and the second inflatable device, wherein the first and the second pleats are capable of expanding on one side relative to another side to enable curving and bending of the catheter body in a vicinity of the first and the second pleats, and wherein the midsection is configured to receive an external clamp.

In a preferred embodiment, the first and the second inflatable device each further comprises: a positioning and guiding member, attached to each of the first and the second inflatable device, for placing each of the first and the second inflatable device at a desired location by an operator.

In another preferred embodiment, the positioning and guiding member comprises: an anchor portion proximate to the inner annulus of each of the first and the second inflatable device, capable of immobilizing an attached inflatable device on the catheter body; and a finger grip portion attached to the anchor portion for easy gripping. In another preferred embodiment, the anchor portion is ring-shaped disposed around the catheter body, and wherein the anchor portion and the finger grip portion are on a side of each of the first and the second inflatable device proximate to the first and the second pleat.

In another preferred embodiment, the at least one obstructing stop comprises at least one of: 1) an adjustable stop, and 2) a fixed stop. In some embodiments, the adjustable stop comprises a groove selected from a plurality of grooves disposed longitudinally around the outer perimeter of the catheter body; and an elastic ring, wherein the groove and the elastic ring are configured such that when the elastic ring is installed in the groove, the elastic ring extends radially outward a sufficient distance to stop the inflatable device from sliding; and wherein the fix stop is affixed to the outer perimeter of the catheter body, and extends radially outward a sufficient distance to stop the inflatable device from sliding The present invention also relates to a system for restoring blood flow to a traumatized blood vessel, comprising: a catheter body, in a tubular shape, comprising: a first and a second tip, each configured to permit insertion into a blood vessel without damaging an inner wall of a blood vessel lumen; a first and a second set of a plurality of fenestrations, disposed proximate to each tip extending a length of the catheter body away from each tip towards a center portion of the tubular catheter body; a first and a second inflatable device, placed circumferentially and longitudinally about the catheter body, configured such that when uninflated each is capable of sliding over a section of the catheter body, and when inflated an inner annulus of each presses against an outer perimeter of the catheter body; a first and a second pleat, spaced apart by a midsection, located in the center portion of the catheter body between the first and the second inflatable device; at least one obstructing stop, located on the outer perimeter of the catheter body in a section longitudinally adjacent to each of the first and the second set of the plurality of fenestrations towards the center portion, to obstruct the first or the second inflatable device from sliding over the first or second set of a plurality of fenestrations proximate to the first or the second tip of the catheter body; a pumping device; a first and a second flexible tube connecting the pumping device with the first and the second inflatable device, respectively, wherein the first and the second pleats are capable of expanding on one side relative to another side to enable curving and bending of the catheter body in a vicinity of the first and the second pleats, wherein the midsection is configured to receive an external clamp, and wherein the pumping device is in fluid communication with the first and the second inflatable device via the first and the second flexible tube, respectively.

The present invention further provides a method for restoring blood flow to a traumatized blood vessel using the catheter assembly of the current invention, comprising the steps of: a) inserting a first tip of a catheter body into a lumen of a first undamaged portion of the traumatized blood vessel so that a first set of a plurality of fenestrations, disposed proximate to the first tip, are inside the first undamaged portion of the traumatized blood vessel; b) positioning a first inflatable device along a first length of the catheter body to a first location proximate to the first undamaged portion of the traumatized blood vessel; c) inserting a second tip of the catheter body into the lumen of a second undamaged portion of the traumatized blood vessel so that a second set of a plurality of fenestrations, disposed proximate to the second tip, are inside the second undamaged portion of the traumatized blood vessel, by bending the catheter body using at least one of a first and a second pleat so that the catheter body conforms to a contour of an injured area, wherein the second undamaged portion of the traumatized blood vessel is separated from the first undamaged portion of the traumatized blood vessel by a damaged portion of the traumatized blood vessel; and d) positioning a second inflatable device along a second length of the catheter body to a second location proximate to the second undamaged portion of the traumatized blood vessel.

In one embodiment, the first and the second inflatable device are uninflated, and the method further comprises a subsequent step of inflating the first and the second inflatable devices with a pumping device.

In another embodiment, the method further comprises a step of holding the catheter body in place by clamping around the midsection.

BRIEF DESCRIPTION OF THE DRAWINGS

For the purpose of illustration, there is shown in the drawing certain embodiments of the present invention. In the drawing, like numerals indicate like elements throughout. It should be understood that the invention is not limited to the precise arrangements, dimensions, and instruments shown. In the drawing:

FIG. 5 is a schematic representation of a system for restoring blood flow to a traumatized blood vessel according to one embodiment of the present invention.

DETAILED DESCRIPTION OF THE INVENTION

Figure 1:
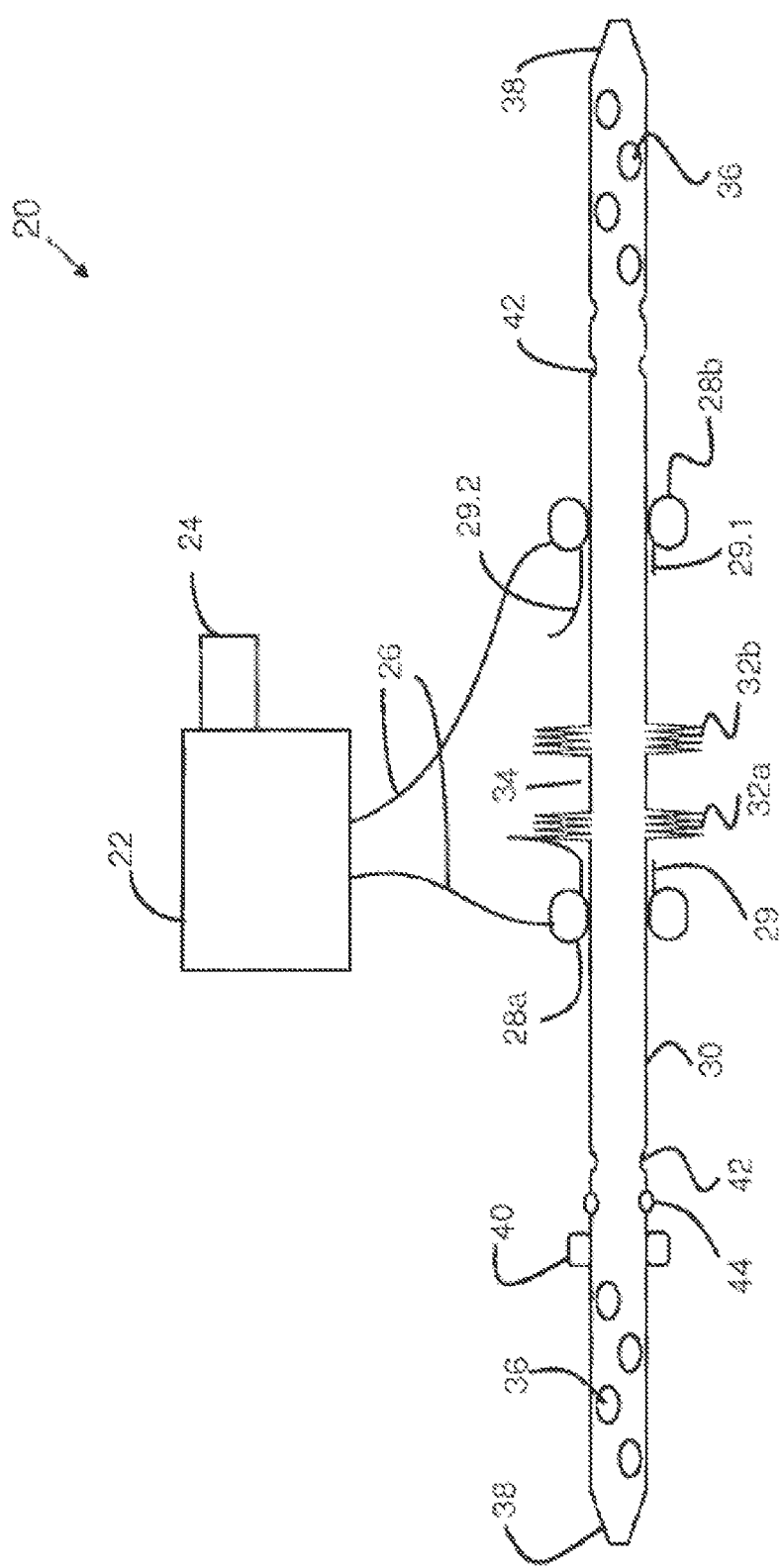
FIG. 1 is a schematic representation of a system for restoring blood flow to a traumatized blood vessel according to one embodiment of the present invention.
Figure 2:
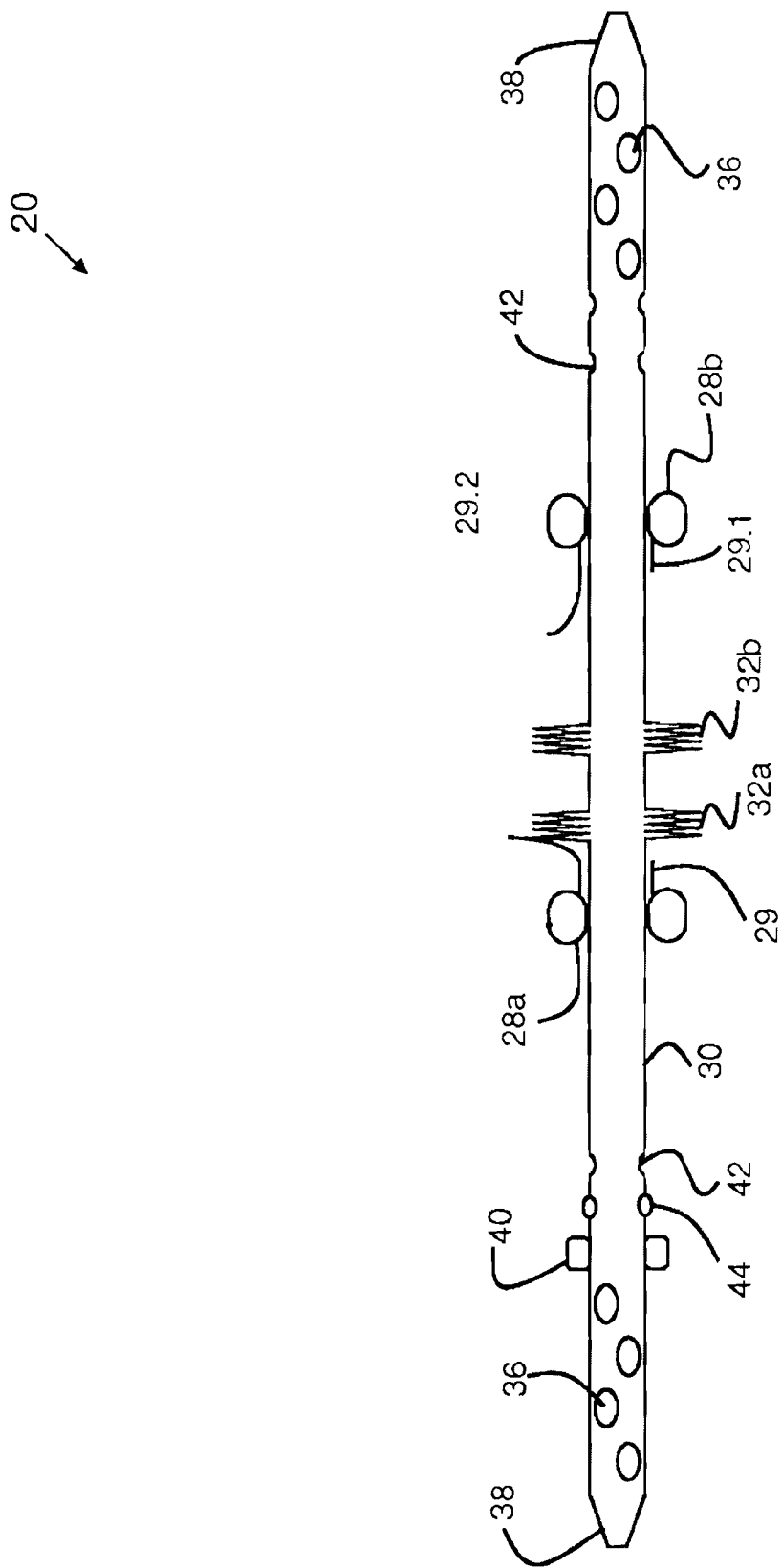
FIG. 2 is a schematic representation of a catheter assembly according to one embodiment of the present invention.
Figure 3:
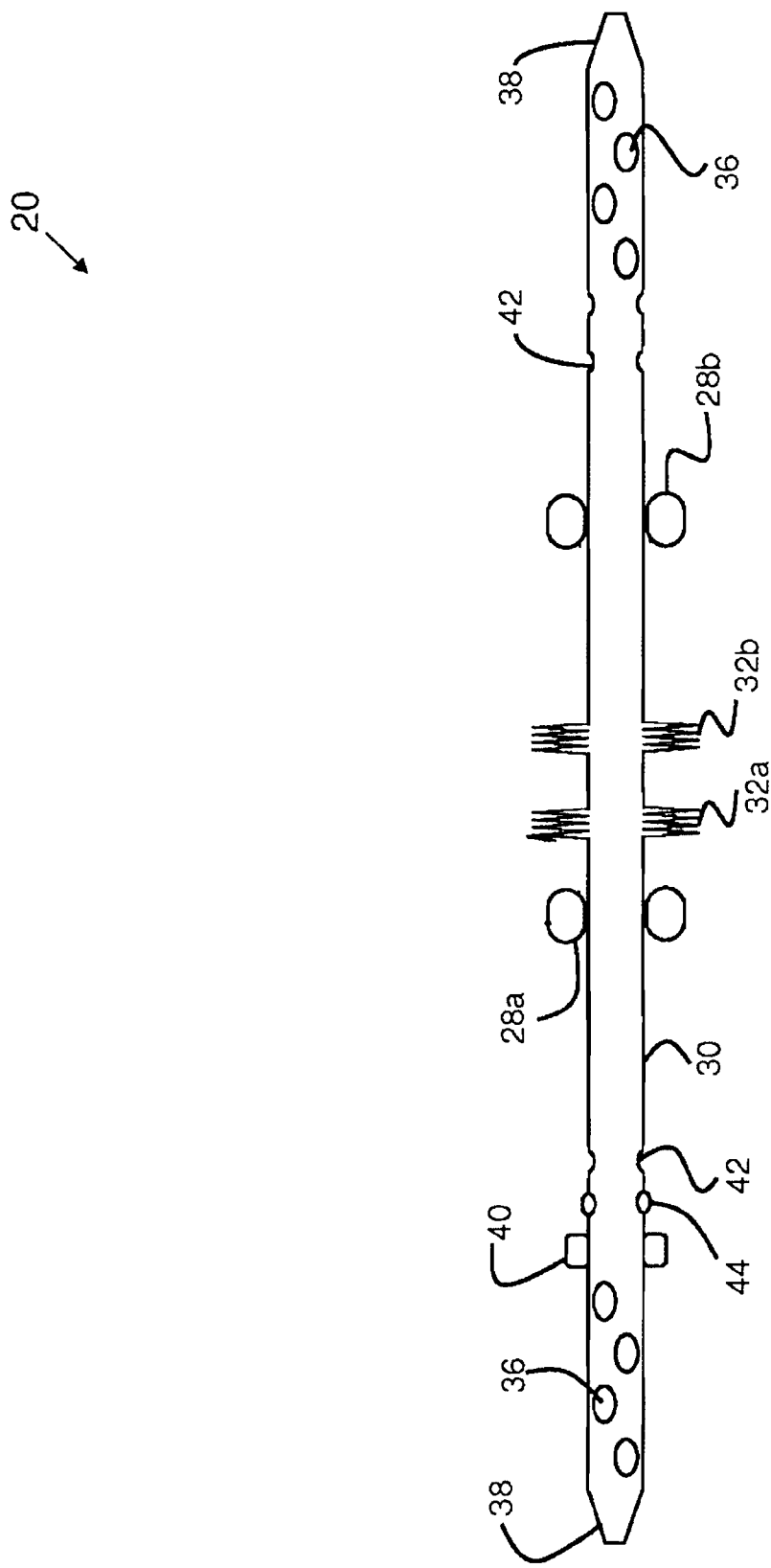
FIG. 3 is a schematic representation of a catheter assembly according to another embodiment of the present invention.

Reference to the drawing illustrating various views of exemplary embodiments of the present invention is now made. In the drawing and the description of the drawing herein, certain terminology is used for convenience only and is not to be taken as limiting the embodiments of the present invention.

FIG. 1 is a schematic representation of a catheter assembly used to restore blood flow to a traumatized blood vessel. Some embodiments of the present invention are used in cases in which the trauma to the body includes an open wound that permits endovascular access to the damaged artery. In other cases, the wall of the artery is damaged, but the arterial tissue both upstream and downstream of the damage is generally intact.

The catheter assembly 20 includes a catheter body 30, generally in a tubular shape, preferably having a pair of inflatable devices such as balloons that can be easily slid along the length of the catheter. A pumping device 22, such as a hand pump, provides a mechanism for pressurizing the balloons after they have been located in their proper positions. The catheter assembly 20 includes a catheter body 30, preferably fabricated from a flexible material, and adapted and configured to fit within a blood vessel of a patient.

Each end of the catheter 30 includes a tip 38 that is configured to permit the end of the catheter to be inserted into a blood vessel without damaging the inner walls of the vessel lumen as the catheter tip 38 is inserted into the vessel. The tips 38 are shown in the shape of a truncated cone, but can be of any shape (such as rounded) to minimize friction or interference with the lumen inner wall. Although the tips 38 are shown on the ends of the catheter 30 with a generally straight, coaxial shape, other embodiments may be utilized. In some embodiments, one or more of the tips 38 are offset to one side so as to permit the user to twist the catheter body 30 within the vessel and preferably guide it to a branch vessel. In yet other embodiments, one or more of the ends of the catheter 30 are curved to facilitate the guidance of the tip 38 into a branching vessel. Further, although the tips 38 are shown as generally closed, other tips may have one or more openings or fenestrations to permit the flow of fluid. In yet other embodiments, the tips 38 are fabricated from a mesh material.

Located proximate to each tip 38 is one or more fenestrations 36 to provide fluid flow (such as blood) in and out of the interior of the catheter 30. The one or more fenestrations 36 extend along a length of the catheter body 30 in a direction from the tip toward the center of the catheter.

Located inwardly from the fenestrations 36 are one or more obstructing stops. These stops prevent the balloons 28a and 28b from sliding over the fenestrated portions of the catheter 30. FIG. 1 shows a fixed stop 40 located on the left side of catheter 30. The fixed stop 40 is affixed to the outer perimeter of the catheter body 30, and extends radially outward a sufficient distance so as to interfere with the movement of the balloon 28a and to stop the balloon 28a from sliding past the fixed stop 40. In some embodiments, the fixed stops 40 are circular rings extending around the circumference of the catheter body 30. In yet other embodiments, the stops 40 can be a single outwardly-extending projection, a pair of projections, or the like.

Other embodiments of the present invention include one or more adjustable stops located inward from the fenestrated ends of the catheter body 30. As seen on the left side of FIG. 1, a ring 44 (such as an o-ring or other elastic ring) is shown located within a groove 42 that extends around the circumference of the catheter body 30. An adjustable stop is formed by the placement of an elastic ring 44 within a groove 42. It can be seen that some embodiments include multiple circumferential grooves 42 among which one is selected to place the ring 44, thereby allowing adjustment of the length of the section of the catheter body 30 on which the uninflated balloon 28a slides. The rings 44 and grooves 42 are adapted and configured such that the outer diameter of the ring 44 when installed in a groove extends radially outward a distance sufficient to interfere with the sliding movement of the balloons 28a and 28b.

The catheter body 30 includes a pair of pleated areas 32a and 32b that are preferably spaced apart by a midsection 34. The pleats 32a and 32b are capable of expanding on one side relative to another side (such as from top to bottom) such that the overall shape of the catheter 30 can be curved or bent in the vicinity of the pleats. The pleats 32a and 32b preferably hold their positions after the catheter is reshaped to the new configuration. In that manner, the catheter body 30 can have a curved shape or an S shape. By using the pleats 32a and 32b in that manner, the overall shape of the catheter body 30 can be adapted to better fit the shape of the traumatized anatomy. And, by better accommodating the traumatized anatomy, the catheter body 30 is more likely to stay in place if the injured patient moves.

In yet other embodiments the pleats 32a and 32b are adapted and configured to serve as finger grips for the emergency technician. In such embodiments it is recognized that the smooth outer diameter of the catheter body 30 may be inadequate for sufficient grip in stressful situations (such as in warfare). In some embodiments, the tips of the pleats 32, as well as their larger diameter, provide improved grip of the catheter body 30 as well as a tactile sense of where the technician's fingers are located along the length of the catheter body 30. In other embodiments, the pleats are replaced with a series of non-expandable ridges or other tactile features.

Preferably located between the pleated areas 32a and 32b, is a mid-section 34, adapted and configured to receive an external clamp. In some embodiments, the midsection 34 has a cylindrical outer shape. In yet other embodiments, the midsection 34 is fabricated with thicker walls for increased strength in compression. In still other embodiments, the midsection 34 can include one or more outward projecting features that are adapted and configured to receive therebetween the ends of a clamp. In some embodiments that don't include pleats, a mid-section 34 that is adapted and configured for clamping can be established by a pair of spaced-apart rings or projections. In that manner, an external clamp can be coupled to the mid-section 34 and also be coupled to the clothing or anatomy of the patient. That external clamp helps maintain the catheter body 30 in a fixed position on the injured patient, especially for those situations in which the patient is being moved and subjected to external disturbances (such as a bumpy road, or handling on a stretcher).

The catheter body 30 is received within the inner circumferences of a pair of balloons 28a and 28b. Preferably, each of the balloons 28a and 28b is generally slidable along the length of the external surface of the catheter body 30. However, in some embodiments, one of balloons 28a and 28b may be fixed to the outer diameter of the catheter body 30 at a specific location. The balloon 28a is located between the pleats 32a and the fixed stop 40. The balloon 28b is located between the pleats 32b and the tip 38. The balloon 28b could be removed from the catheter body 30, whereas the balloon 28a is captured within a portion of the length of the catheter body 30. In their uninflated states, the balloons 28a and 28b slide easily over their respective portions of the catheter body 30.

In some embodiments, each of the balloons 28a and 28b includes a positioning and guiding member 29 attached to the balloon, and in some cases, integrally molded with the balloon. That positioning and guiding member 29 has sufficient rigidity to be used by the emergency technician for placing a balloon 28a or 28b at the desired location. It is recognized that in some situations the trauma is such that the positioning of balloon 28a or 28b may be a blind positioning, in which case the positioning and guiding members 29 are used to assist in positioning the balloon, even though the balloon cannot be seen.

In some embodiments, the positioning and guiding member 29 includes an anchor portion 29.1 (e.g. cylindrical or ring-shaped) that is coupled to a balloon 28a or 28b proximate to the inner periphery (or annulus) of the balloon. Preferably, the anchor portion 29.1 has a ring shape of sufficient rigidity so as to uniformly impart the sliding load applied by the emergency technician into the balloon. Located at the inner ends of the anchor portion 29.1 proximate to the pleats is a flexible finger grip 29.2, adapted and configured to be easily pinched by the fingers of the technician, and further to impart the load from the physician's finger into the anchor portion 29.1. The technician uses the finger grip 29.2 to move the balloons along the length of the catheter body 30. As shown with the left side balloon 28a, the finger grip 29.2 is sufficiently flexible (shown in the Figure as being deflected by the pleats 32a) so as to not interfere with the operation of the catheter assembly 20, yet rigid enough to withstand a compressive load applied by the technician without buckling. The cross sectional shape of the finger grip 29.2 may be circular (corresponding to a rod-like projection) or a sector of a circle (such as a thin plate coupled to a circumferential sector of the guiding feature 29.1), as examples.

The balloons 28a and 28b can be inflated with a gas or a liquid (such as saline) and each is connected by a flexible tube 26 that provides fluid communication with a source of pressure, such as a pumping device 22. Pressure (such as air pressure) can be applied by the pumping device 22 through conduits, such as the flexible tube 26, so as to inflate the balloons 28a and 28b. In one embodiment, the pumping device is adapted with ports for the conduits and an infusion device. In another embodiment, one of the ports allows deployment of the device over a wire.

When inflated, the balloons 28a and 28b tighten their inner annulus against the outer perimeter of the catheter body 30 so as to form a generally leakproof seal. In their inflated state, the balloons 28a and 28b are maintained at a fixed position on the catheter body 30 by friction. It is understood that in some embodiments, either the inner surface of the balloons 28 and/or the outer perimeter of the catheter body 30 can be treated to have increased friction. Examples of such treatment include coatings (such as the coatings used to form tamper-evident regions on flexible recloseable containers). Yet another example of such treatments is physical impressions or projections, such as a cross-hatch pattern, a pattern of rings, a pattern of sawtooth teeth, or others.

In some embodiments, the source of pressure is a pumping device 22 adapted and configured to be operated by a single hand of an emergency technician. As the technician grabs the pumping device 22 and squeezes it, air pressure is provided by conduits, such as the flexible tube 26, into the balloons 28a and 28b, thereby causing them to expand. Preferably, both of the flexible tubes 26 are attached to a single source of pressure (the pumping device 22), which minimizes the amount of equipment that an emergency technician must cope with while treating the injured patient. In some embodiments, the pressure source includes a relief valve 24 that releases pressure in the balloons 28a and 28b so as to prevent overexpansion, distortion or rupture of the balloons.

Figure 4:
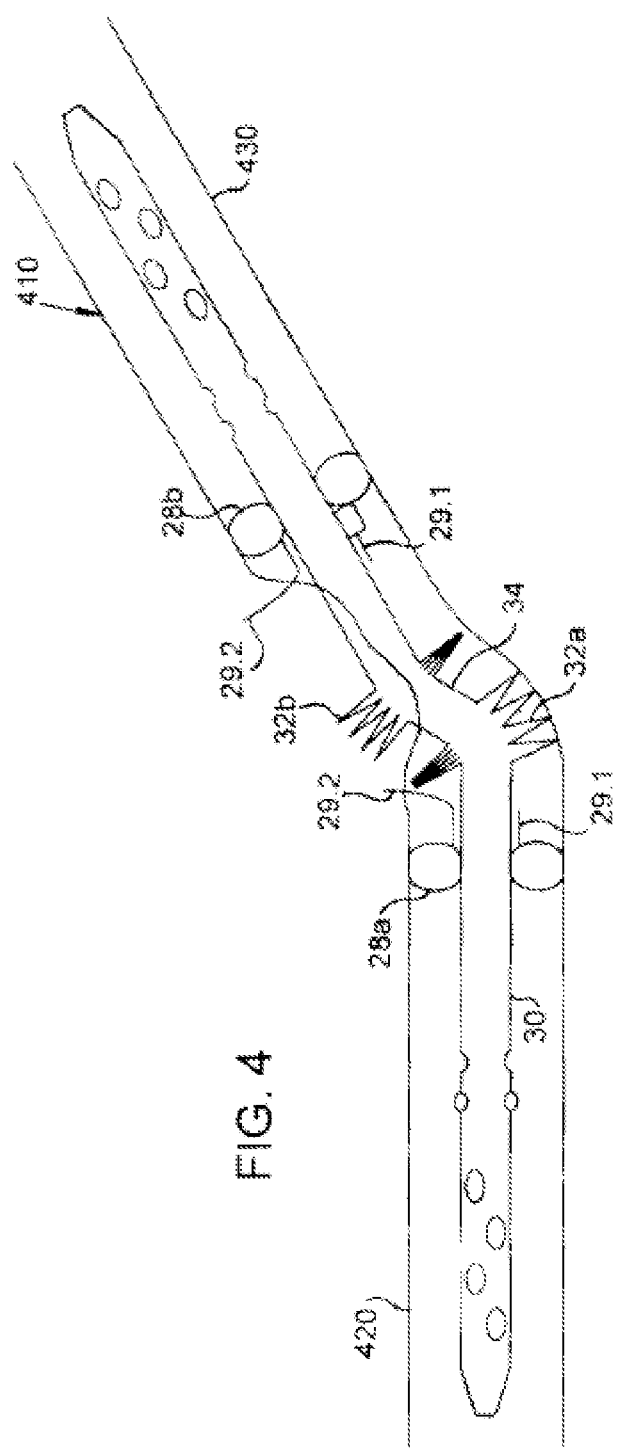
FIG. 4 is a schematic representation of a catheter assembly according to another embodiment of the present invention.

During use, the emergency technician locates the bleeding artery in the patient's wound. The technician then advances the first tip of the catheter body within the damaged artery 41 until a first balloon 28a is located proximate to a first undamaged portion of the traumatized artery 42, as shown in FIG. 4. In some embodiments, the pumping device 22 includes a switch or valve that permits the technician to expand the first balloon during this phase of partial insertion. In yet other embodiments, both balloons are expanded simultaneously.

After the first end of the catheter body 30 is inserted within the artery and the first balloon 28a (whether inflated or deflated) is positioned proximate to the undamaged tissue with the aid of the finger grip 29.2, the position of the first balloon 28a is immobilized by the anchor portion 29.1. The technician then places the second tip of catheter body 30 into the lumen of the damaged artery. By handling the finger grip

29.2, the technician positions the second balloon 28b along the length of the catheter body 30 to a location that is proximate to a second undamaged portion of the traumatized artery. The second balloon 28b is immobilized in a like manner as the first balloon 28a using the anchor portion 29.1. The second balloon 28b is inflated with pumping source 22 (or alternatively, both balloons are inflated at this time). As the second end of the catheter is inserted into the lumen of the damaged artery, the technician bends or curves the catheter body 30 by way of the pleats 32 so as to best accommodate the shape of the injury and the location of the damaged artery. As the catheter body 30 is being situated within the damaged artery, the technician can use a clamp (not shown) around the midsection 34 to securely hold the catheter body 30 in place. This clamp can then be coupled (such as by tape) to the anatomy of the patient.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

These and other advantages of the present invention will be apparent to those skilled in the art from the foregoing specification. Accordingly, it is to be recognized by those skilled in the art that changes or modifications may be made to the above-described embodiments without departing from the broad inventive concepts of the invention. It is to be understood that this invention is not limited to the particular embodiments described herein, but is intended to include all changes and modifications that are within the scope and spirit of the invention.

What is claimed is:

1. A catheter assembly for restoring blood flow to a traumatized blood vessel, comprising:
    a tubular catheter body including a first and a second tip and a center portion, each tip configured to permit insertion into a blood vessel;
    a first plurality of fenestrations disposed proximate to the first tip and a second plurality of fenestrations disposed proximate to the second tip;
    a first inflatable device and a second inflatable device, configured such that when uninflated each inflatable device is capable of sliding over a section of the catheter body, and when inflated an inner annulus of each inflatable device presses against an outer perimeter of the catheter body;
    a first pleat located in the center portion of the catheter body between the first and the second inflatable device, wherein the first pleat is capable of expanding on a first side relative to a second side to enable curving or bending of the tubular catheter body in a vicinity of the first pleat; and
    a first obstructing stop positioned between the first plurality of fenestrations and the first pleat and configured to obstruct the first or the second inflatable device from sliding over the first plurality of fenestrations.

2. The catheter assembly of claim 1, further comprising: a first positioning and guiding member attached to the first inflatable device and a second positioning and guiding member attached to the second inflatable device, wherein each positioning and guiding member includes an anchor portion proximate to the inner annulus of the respective first or second inflatable device capable of immobilizing the respective inflatable device on the catheter body, and a finger grip portion attached to the anchor portion.

3. The catheter assembly of claim 1, wherein the first obstructing stop comprises a fixed stop affixed to an outer perimeter of the catheter body, the fixed stop extending radially outward to stop the first inflatable device from sliding past the fixed stop.

4. The catheter assembly of claim 1, further comprising:
    a plurality of grooves disposed longitudinally around the outer perimeter of the catheter body; and
    an elastic ring, configured to be installed in one of the plurality of grooves such that when the elastic ring is installed in the groove, the elastic ring extends radially outward a sufficient distance to stop the inflatable device from sliding past the fixed stop.

5. The catheter assembly of claim 1, further comprising a second pleat spaced apart from the first pleat by a midsection, wherein the second pleat is capable of expanding on a first side relative to a second side to enable curving or bending of the tubular catheter body in a vicinity of the second pleat.

6. The catheter assembly of claim 5, further comprising a second obstructing stop positioned between the second plurality of fenestrations and the second pleat and configured to obstruct the second inflatable device from sliding over the second plurality of fenestrations.

7. The catheter assembly of claim 5, wherein the midsection is configured to receive an external clamp.

8. The catheter assembly of claim 1, wherein the first and second plurality of fenestrations are configured to provide fluid flow in and out of an interior of the catheter body.

9. The catheter assembly of claim 1, wherein each of the first inflatable device and the second inflatable device is configured to be in fluid communication with a source of pressure to inflate each of the first inflatable device and the second inflatable device.

10. The catheter assembly of claim 9, wherein the source of pressure is configured to simultaneously inflate the first inflatable device and the second inflatable device.

11. The catheter assembly of claim 1, wherein the first tip is offset to a first side.

12. The catheter assembly of claim 1, wherein the tubular catheter body is curved.

13. The catheter assembly of claim 1, wherein the first tip includes one or more fenestrations or is fabricated from a mesh material.

14. The catheter assembly of claim 1, wherein, when inflated, the inner annulus of each inflatable device forms a generally leakproof seal with the catheter body.

15. The catheter assembly of claim 1, wherein at least one of an interior surface of each inflatable device and an outer perimeter of the catheter body includes a coating, a physical impression, or a projection to increase friction between the inflatable device and the catheter body.

16. A system for restoring blood flow to a traumatized blood vessel, comprising:
    a tubular catheter body including a first tip and a second tip, each tip configured to permit insertion into a blood vessel;
    a first plurality of fenestrations disposed proximate to the first tip and a second plurality of fenestrations disposed proximate to the second tip;
    a first inflatable device and a second inflatable device, configured such that when uninflated each inflatable device is capable of sliding over a section of the catheter body, and when inflated an inner annulus of each inflatable device presses against an outer perimeter of the catheter body;
    a first and a second pleat, spaced apart by a midsection, located in the center portion of the catheter body between the first and the second inflatable device, wherein the first pleat is capable of expanding on a first side of the first pleat relative to a second side of the first pleat to enable curving and bending of the catheter body in a vicinity of the first pleat and wherein the second pleat is capable of expanding on a first side of the second pleat relative to a second side of the second pleat to enable curving and bending of the catheter body in a vicinity of the second pleat;

a first obstructing stop and a second obstructing stop, the first obstructing stop positioned between the first plurality of fenestrations and the first pleat and configured to obstruct the first inflatable device from sliding over the first plurality of fenestrations, the second obstructing stop positioned between the second plurality of fenestrations and the second pleat and configured to obstruct the second inflatable device from sliding over the second plurality of fenestrations; and a pumping device in fluid communication with each of the first inflatable device and the second inflatable device, wherein the pumping device is configured to inflate each of the first inflatable device and the second inflatable device.

17. A method for restoring blood flow to a traumatized blood vessel using a catheter assembly, comprising the steps of:

a. inserting one of a first tip and a second tip of a catheter assembly into a lumen of a first undamaged portion of the traumatized blood vessel such that a first plurality of fenestrations or a second plurality of fenestrations are inside the first undamaged portion of the traumatized blood vessel, the catheter assembly including:

a tubular catheter body including the first tip, a second tip, and a center portion, the first plurality of fenestrations being disposed proximate to the first tip and the second plurality of fenestrations being disposed proximate to the second tip;

a first inflatable device and a second inflatable device, configured such that when uninflated each inflatable device is capable of sliding over a section of the catheter body and when inflated an inner annulus of each inflatable device presses against an outer perimeter of the catheter body;

a first-pleat located in the center portion of the catheter body between the first and the second inflatable device, wherein the first pleat is capable of expanding on a first side relative to a second side to enable curving or bending of the tubular catheter body in a vicinity of the first pleat and a first obstructing stop positioned between the first plurality of fenestrations and the first pleat and configured to obstruct the first inflatable device from sliding over the first plurality of fenestrations;

b. positioning the first inflatable device along a first length of the catheter body to a first location proximate to the first undamaged portion of the traumatized blood vessel;

c. inserting the second tip of the catheter body into the lumen of a second undamaged portion of the traumatized blood vessel wherein the second undamaged portion of the traumatized blood vessel is separated from the first undamaged portion of the traumatized blood vessel by a damaged portion of the traumatized blood vessel so that the other of the first plurality of fenestrations and the second plurality of fenestrations are inside the second undamaged portion of the traumatized blood vessel by bending the catheter body using the first pleat so that the catheter body conforms to a contour of an injured area; and d. positioning the second inflatable device along a second length of the catheter body to a second location proximate to the second undamaged portion of the traumatized blood vessel.

18. The method for restoring blood flow to a traumatized blood vessel of claim 17, wherein step a is performed over a wire.

19. The method for restoring blood flow to a traumatized blood vessel of claim 17, wherein the first inflatable device in step b and the second inflatable device in step d are uninflated, and further comprising a subsequent step of:

e. inflating the first and the second inflatable devices with a pumping device in fluid communication with each of the first inflatable device and the second inflatable device.

20. The method for restoring blood flow to a traumatized blood vessel of claim 19 wherein the midsection is configured to receive an external clamp, the method further comprising a subsequent step of:

f. holding the catheter body in place by clamping around the midsection.

* * * * *